US008382760B2

(12) United States Patent
Mantovani et al.

(10) Patent No.: US 8,382,760 B2
(45) Date of Patent: Feb. 26, 2013

(54) INTERMARROW NAIL TO BE INSERTED INTO A FRACTURED LONG BONE

(75) Inventors: Matteo Mantovani, Bussolengo (IT); Michele Coati, San Pietro in Cariano (IT); Graziano Rossi, Verona (IT)

(73) Assignee: Orthofix S.r.l. (IT)

( * ) Notice: Subject to any disclaimer, the term of this patent is extended or adjusted under 35 U.S.C. 154(b) by 49 days.

(21) Appl. No.: 12/997,838

(22) PCT Filed: Jun. 15, 2009

(86) PCT No.: PCT/IT2009/000262
§ 371 (c)(1),
(2), (4) Date: Feb. 18, 2011

(87) PCT Pub. No.: WO2009/150691
PCT Pub. Date: Dec. 17, 2009

(65) Prior Publication Data
US 2011/0137312 A1 Jun. 9, 2011

(30) Foreign Application Priority Data

Jun. 13, 2008 (EP) .................................... 08425423

(51) Int. Cl.
*A61B 17/72* (2006.01)
(52) U.S. Cl. ............................ 606/63; 606/62; 606/64
(58) Field of Classification Search ............... 606/62–64
See application file for complete search history.

(56) References Cited

U.S. PATENT DOCUMENTS

| 4,622,959 | A | * | 11/1986 | Marcus | 606/64 |
| 4,827,917 | A | * | 5/1989 | Brumfield | 606/64 |
| 2007/0123878 | A1 | * | 5/2007 | Shaver et al. | 606/64 |

FOREIGN PATENT DOCUMENTS

| DE | 20 2005 020788 U1 | 7/2006 |
| EP | 0882431 A1 | 12/1998 |
| EP | 1815813 A2 | 8/2007 |
| EP | 1 905 367 A1 * | 4/2008 |
| JP | 10 057398 A | 3/1998 |
| JP | 10057398 * | 3/1998 |
| WO | 2005/094705 A2 | 10/2005 |

* cited by examiner

*Primary Examiner* — Eduardo C Robert
*Assistant Examiner* — Julianna N Harvey
(74) *Attorney, Agent, or Firm* — Akerman Senterfitt

(57) ABSTRACT

The invention concerns an intramedullary nail to be inserted into a fractured long bone, for example a femur, comprising: a rod (2) extending between a proximal part (3) and a distal part (4); a tubular sleeve (5) into which said rod (2) is inserted coaxially; at least a first pair of expansion means (12) located in the distal part (4) of said rod (2), said expansion means (12) being made of a shape-memory material in order to assume a first configuration of rest in which they are disposed inside recesses in the lateral wall of the nail (1), and a second configuration of use in which said means (12) are located projecting from the lateral wall of the nail (1); slots (55) are present on the tubular sleeve (5) in correspondence with the shape-memory means (12) to allow for the fastening onto the bone when the means assume said second configuration of use; where said rod (2) comprises in correspondence with the proximal end (3) a transversal channel (6) for the passage of a stop screw (S), said tubular sleeve (5) comprising a pair of opposite apertures (7a, 7b) placed in alignment with said channel (6); and where the distal part (4) of the rod (2) does not have any through-channel for a screw.

10 Claims, 11 Drawing Sheets

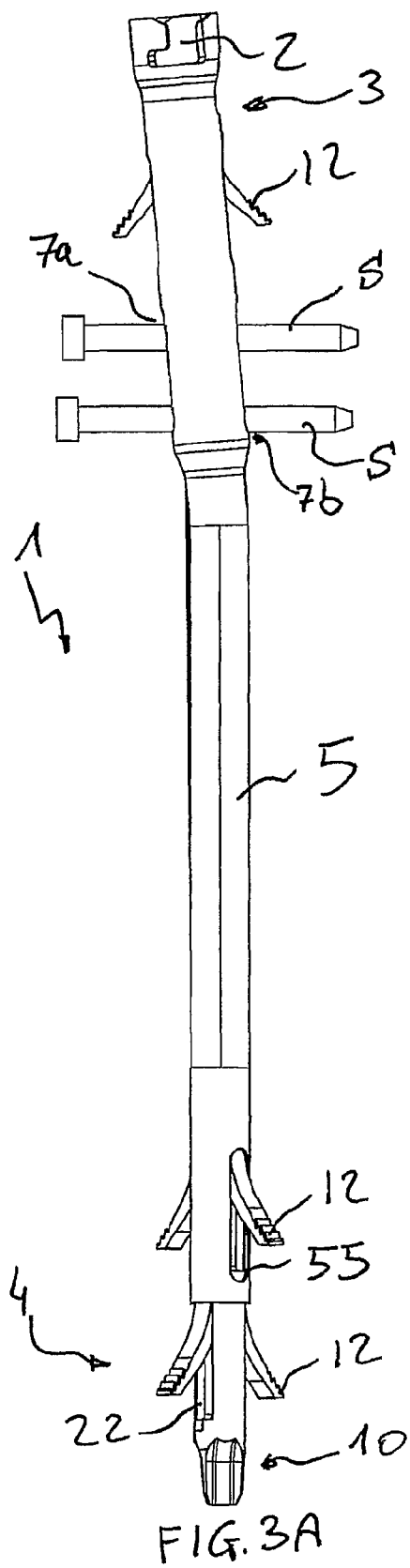
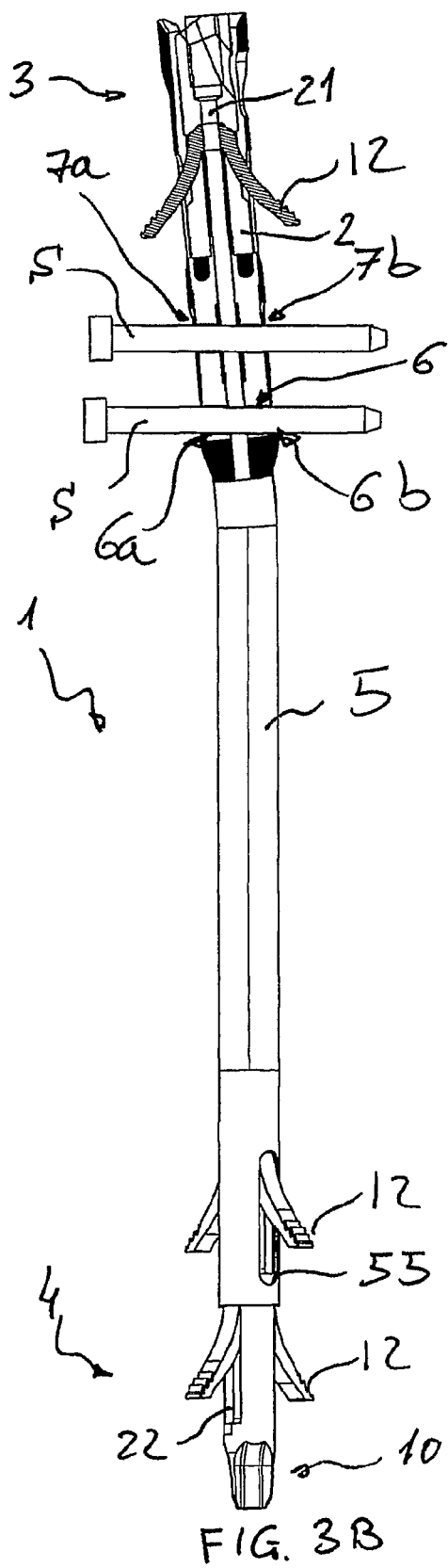
FIG. 3A
FIG. 3B

INTERMARROW NAIL TO BE INSERTED INTO A FRACTURED LONG BONE

FIELD OF APPLICATION

The present invention refers, in its most general aspect, to an intramedullary nail to be inserted into a fractured long bone, for example a femur or a tibia, of the type comprising a cannulated rod extending between a proximal end and a distal end.

PRIOR ART

Intramedullary nails are known that are inserted into a fractured long bone in surgical interventions and are fixed in it, so as to reform the original shape of the bone itself and, at the same time, to restore consistency to the bone so that the bone callus regeneration mechanism can take place correctly.

The rods of such intramedullary nails are generally substantially cylindrical in shape and can be either solid or hollow, in other words cannulated.

In order to fix the intramedullary nail to the bone portions to be reset, two or more staggered holes are usually foreseen on the nail, whose axes lie on parallel or intersecting planes that extend diametrically through the entire rod, at the distal end of the nail itself, and two or more staggered holes of the same size, with axes not necessarily lying on parallel planes, at the proximal end of the nail. Said holes are intended to house bone screws, which are inserted, after suitable drilling in the bone itself, with the result of fixing the intramedullary nail to the bone portions.

Whilst advantageous from many points of views, such known nails do however have some acknowledged drawbacks that are still to be overcome.

The main drawback is that the pinless device of the state of the art does not ensure complete stabilisation of the nail in the leg against the high axial stress that the leg is subjected to in the direction of the medullary canal, which is determined by the weight of a patient's body.

In cases where such stress is applied the nail becomes unstable, causing the bone fragments to become unstable and compromising the process of osteosynthesis, as well as causing anomalies in the healing process, bone dysmetria and rotation of the limb.

Therefore it is necessary that fastening screws are inserted into both the proximal and the distal parts of the nail.

This way of operation presents inevitable inconveniences especially due to the necessity of having to form passages in the body in order to be able to insert the screws themselves.

In order to simplify the operation of fixing the nail in the bone, the use of cannulated nails is proposed that have suitable shape-memory fastening elements on the distal and proximal parts that attach themselves to the bone. An example of such a nail is described in EP 1740113 by the same applicant.

Although these nails with shape-memory elements perform their function of stabilizing the nail in the bone fairly well, especially in the case of less pronounced fractures, their use may not always be recommended in certain circumstances.

Therefore, where it is not possible to use nails with shape-memory elements, use is made of traditional nails that entail the use of fastening screws both in the proximal and in the distal parts, reproducing in that manner the above-mentioned inconveniences.

As a result there is a great need for intramedullary nails of the cannulated type that can be inserted into a long bone, where axial and torsional fixation are guaranteed while remaining a simple and reasonable constructive solution.

The object of the present invention is to provide a solution to the above-mentioned need while at the same time countering the aforementioned invonveniences of the prior art.

SUMMARY OF THE INVENTION

Based upon this idea for a solution, the technical problem is solved according to the invention by a nail as defined in claim 1.

The main advantage of the present invention is that it has a direct blocking of the nail in the bone at the proximal end, which offers a distribution of the axial stress in the proximal area and therefore improved stability of the nail.

Further characteristics and advantages of the osteosynthesis device according to the invention shall become even clearer from the following description of an example embodiment thereof, given for indicating and not limiting purposes with reference to the attached drawings.

BRIEF DESCRIPTION OF THE DRAWINGS

FIGS. 1A-5A illustrate a side view of a nail in its different embodiments respectively, according to the present invention;

FIGS. 1B-5B illustrate a side view of the nail of FIGS. 1A-5A respectively, with the proximal part shown in cross section;

Figure 1A:
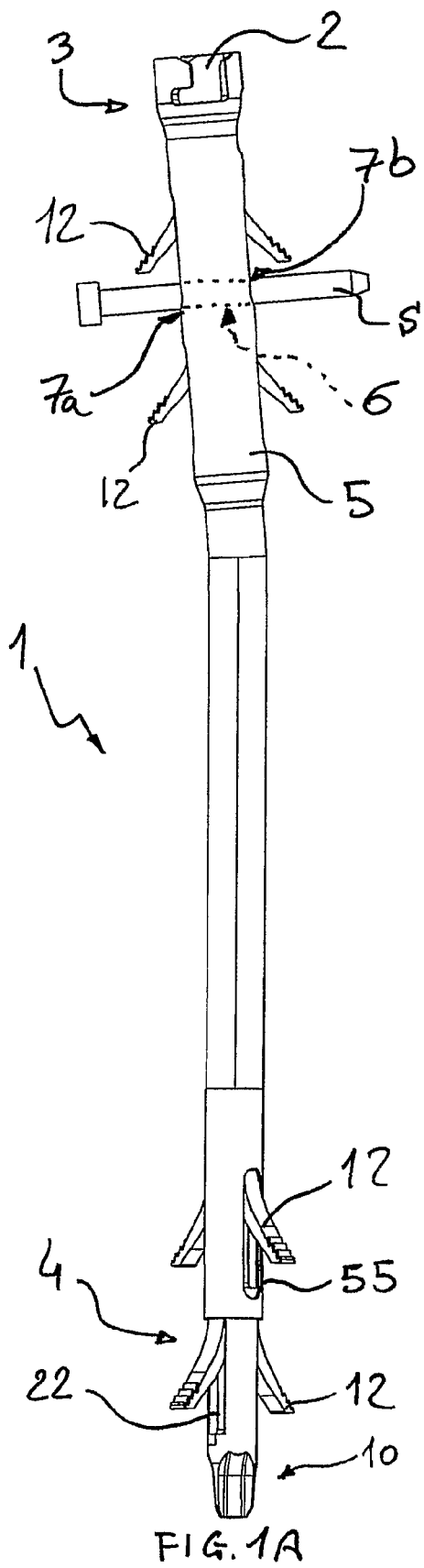

With reference to the aforementioned figures, 1 generally indicates an intramedullary nail in accordance with the present invention, intended to be inserted into a fractured long bone, such as, for example, a femur.

The nail 1, in its general conception, comprises a rod 2 extending between a proximal part, indicated by 3, and a distal part, indicated by 4, and a tubular sleeve 5, in which the rod 2 is inserted coaxially. Said rod 2 in the example is of the cannulated type, i.e. it has an internal cavity, indicated by 21, and extends for at least a portion along a longitudinal axis, indicated with X.

The nail 1 further presents at least a first pair of expansion means located in the distal part 4 of the nail 1. Each of the expansion means in the example consist more specifically of a pair of fins 12 made of a shape-memory material (e.g. Nitinol) already known to the field. Said fins 12 are affixed to the rod 2 and due to their particular material they can assume different configurations.

More precisely, in a first configuration in which the fins 12 are retracted, they are arranged in recesses 22 on the rod 2, whereas in a second configuration of use they are arranged projecting from the rod 2 as demonstrated in the figures.

The passage from the first configuration to the second configuration happens with a rise in temperature. Typically body temperature allows the fins to deform themselves to assume the configuration of use.

In correspondence with the fins 12 the tubular sleeve 5 is provided with suitable slots 55 through which the fins 12 can project freely when transforming from the first to the second configuration in order to attach themselves to the bone in which the nail 1 is inserted.

In accordance with the present invention, the rod 2 comprises in correspondence with the proximal end 3 a transversal channel 6 that extends from an inlet 6a to an outlet 6b for the passage of a stop screw S.

The tubular sleeve 5 is provided with a pair of opposite openings 7a, 7b, respectively an inlet and an outlet, that are placed in correspondence respectively with the the inlet 6a and the outlet 6b of the channel 6 in such a manner as to be in alignment with it.

Naturally, since the rod 2 of the illustration is of the cannulated kind with a hollow space that extends longitudinally all along its extension, the channel 6 will consist of two channel portions that are aligned with the cavity 21 of the rod placed between them. Channel is therefore intended to refer in this case to the assembly that is formed by the two aligned channel portions that form a unique passage for the screw S.

In order to provide a better structural resistance of the rod 2, the distal end 4 lacks a through-channel for a screw, different from the proximal end 3.

In order to improve the fastening properties of the nail to the bone it is possible to apply the fins 12 also in the proximal area 3 of the rod 2, as demonstrated by the figures, as long as their position does not interfere with the passage of the screw S along the channel 6.

Moreover it is possible to provide for the realisation of a rod 2 that contains in the proximal part 3 two channels 6 for the passage of two screws S side by side (FIGS. 2-5).

Figure 1B:
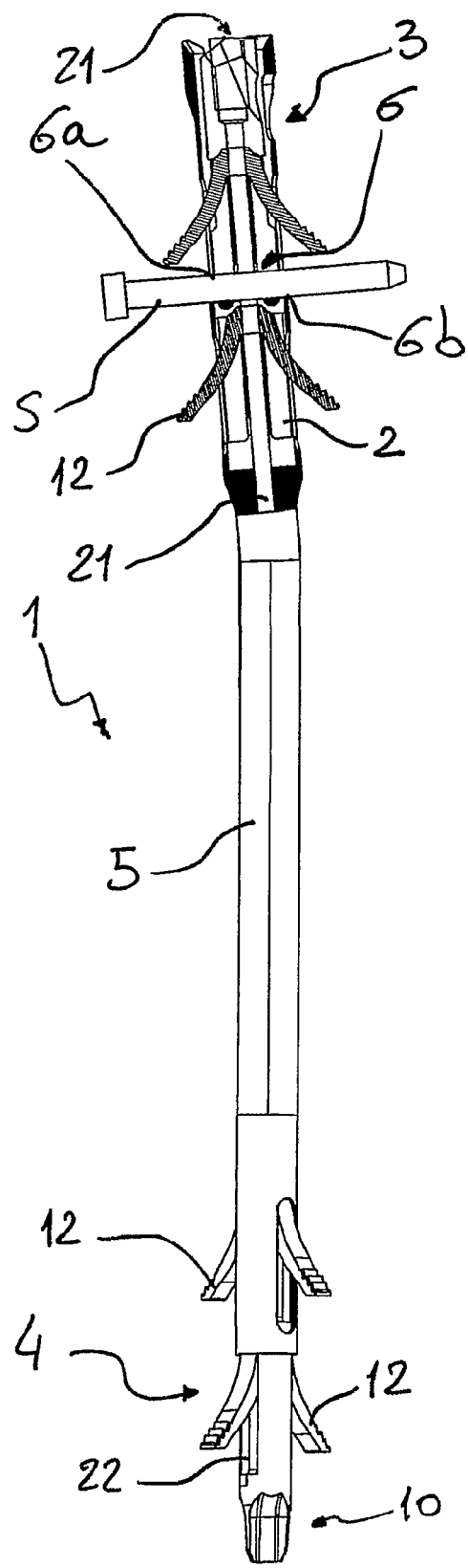
Figure 1C:
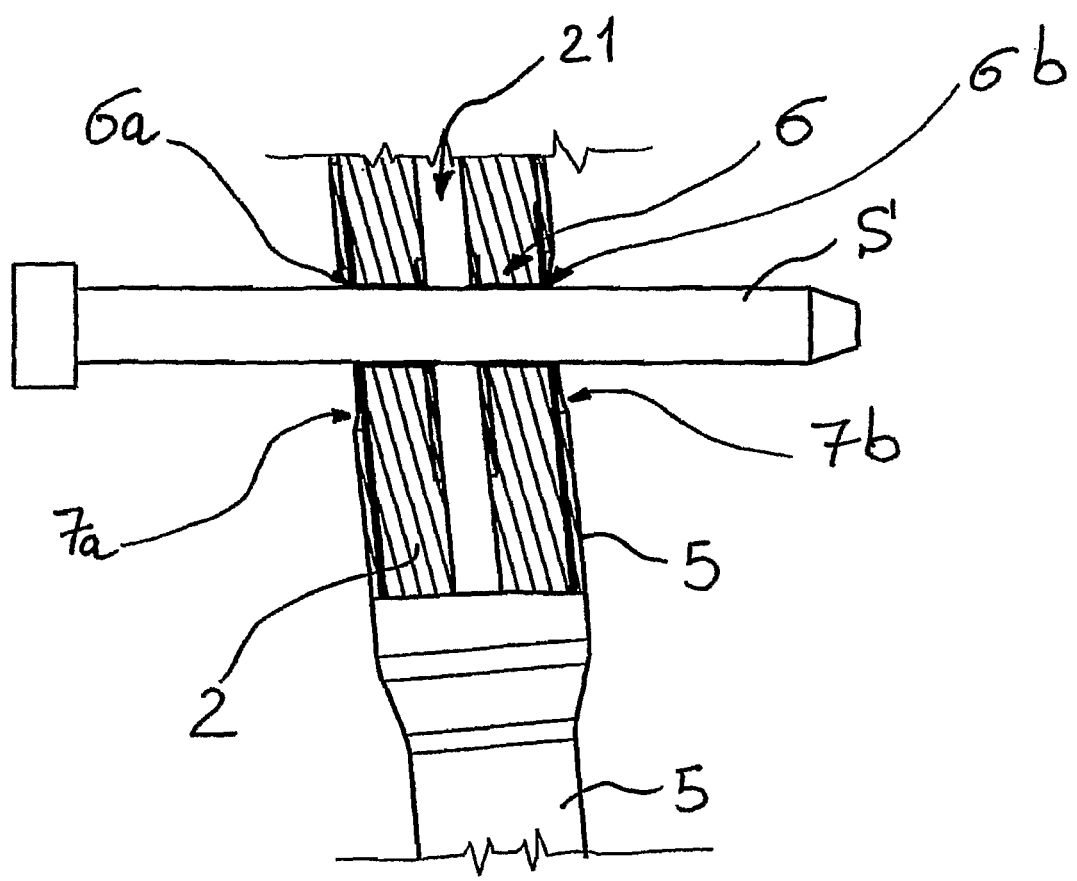
FIG. 1C shows a detail of the connection of the screw in the nail of FIG. 1, with the expansion means omitted.
Figures 2A, 2B:
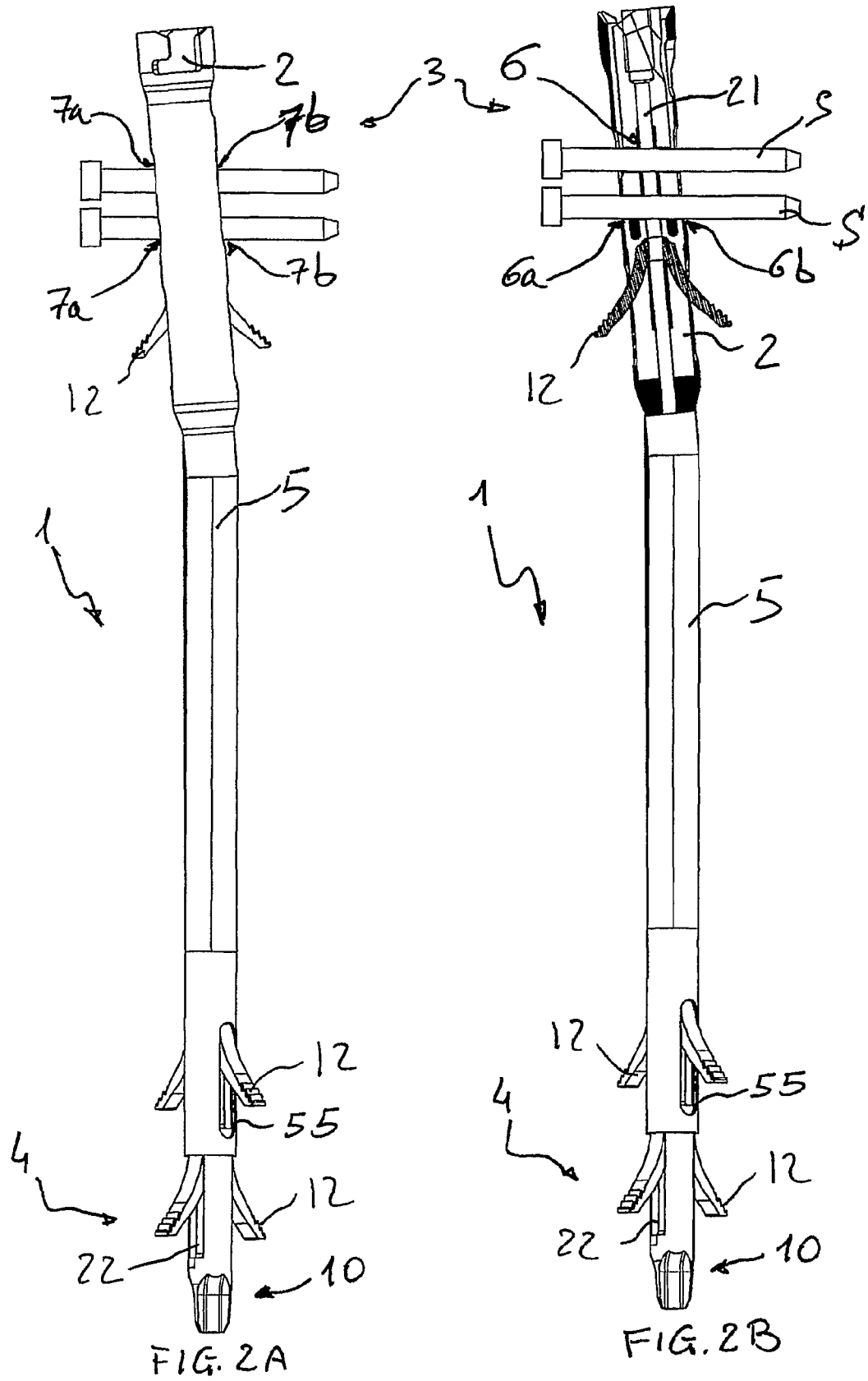

In short, a number of embodiments are possible according to the present invention. For instance, it is possible to have:
- a nail with two pairs of fins 12 in the proximal part 3 with the channel 6 for the passage of the screws placed between the two pairs (FIG. 1);
- a nail with a single pair of fins 12 in the proximal part 3 and two channels 6 for the passage of two screws, where the two channels may be located side by side and placed above the fins (FIGS. 2, 4) or below the pair of fins 12 (FIGS. 3, 5).

Also the inclination of the channel may be chosen in accordance with preference and necessity.

Figure 4A:
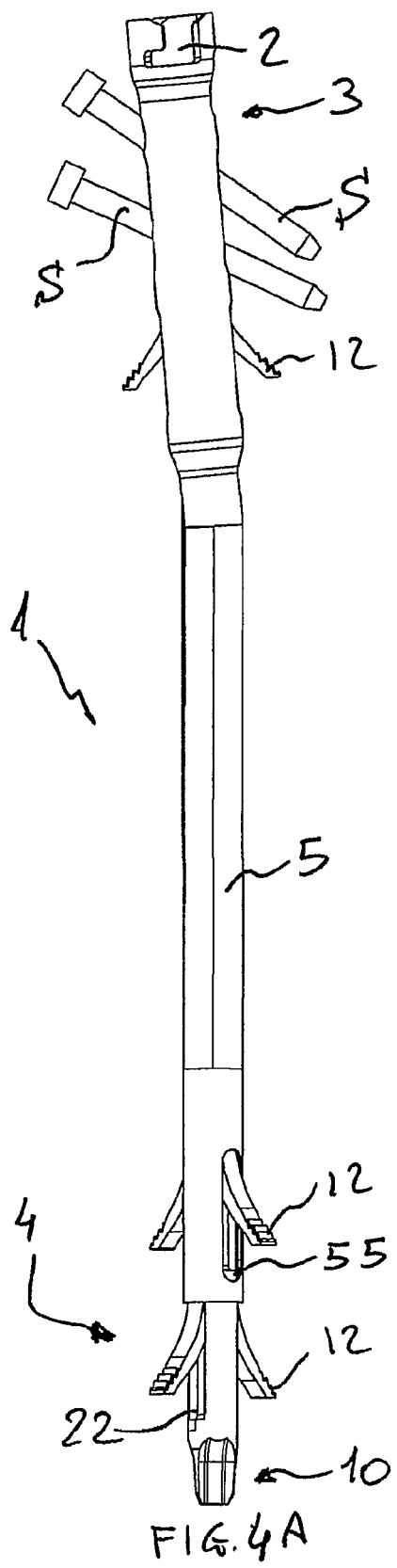
Figure 4B:
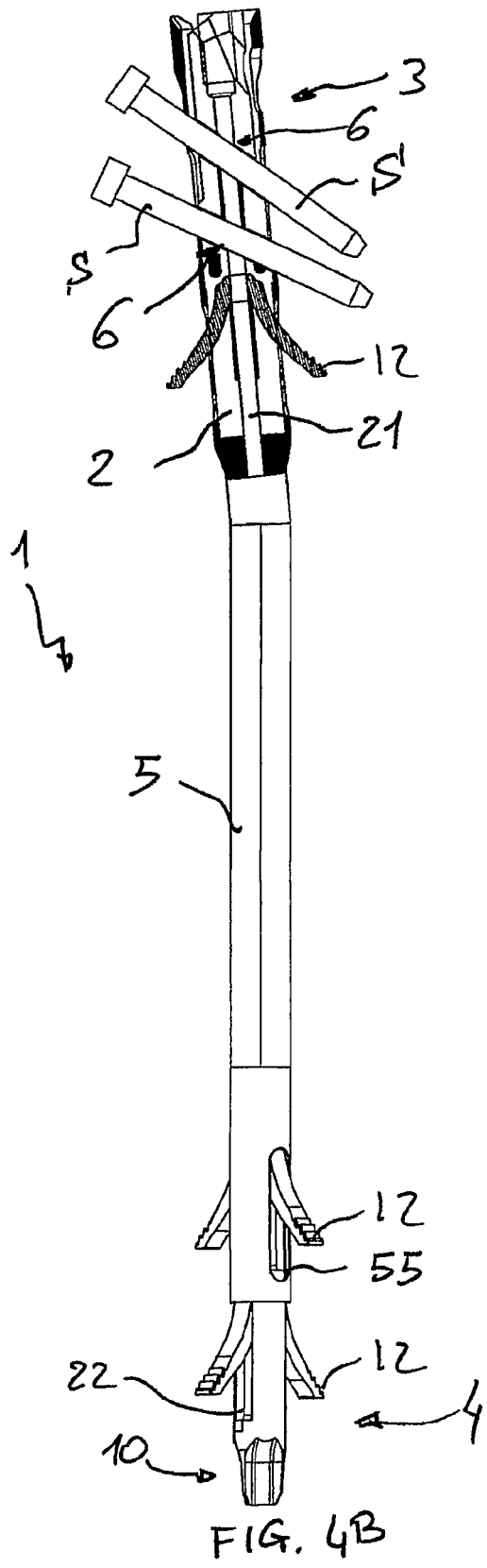
Figure 5A:
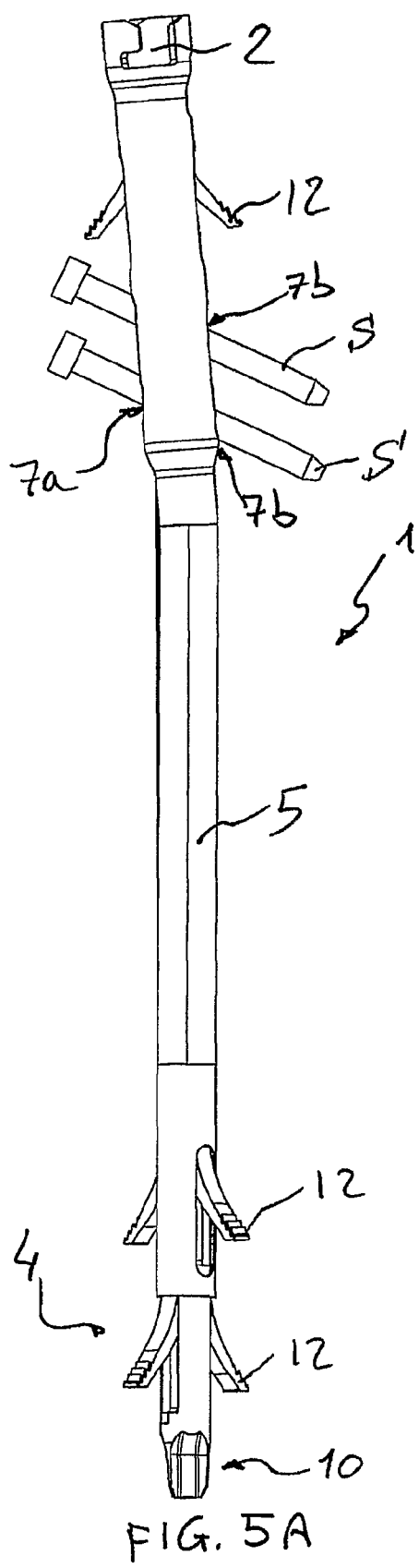
Figure 5B:
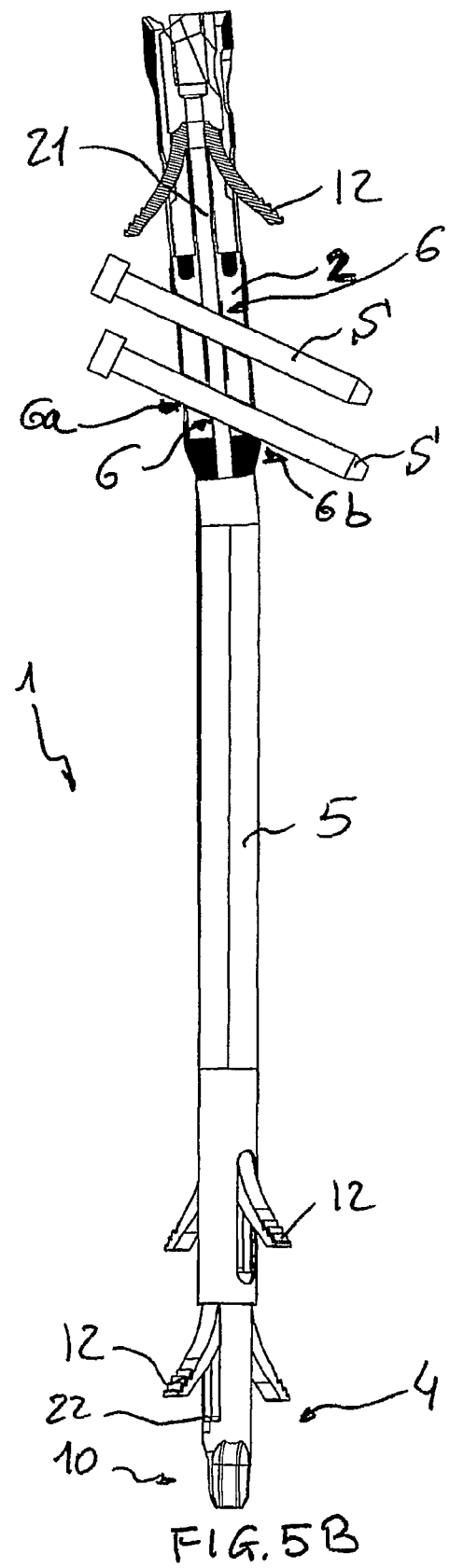

It is therefore possibe to have an embodiment with a channel that is extended substantially perpendicular to the axis of the rod (FIGS. 2, 3) or to have alternative embodiments in which the channel is extended along an axis that is at an acute angle to the longitudinal axis of the rod (FIGS. 4,5).

In order to make the forward insertion of the nail easier during an operation, the nail 1 is shaped so as to follow the natural curvature of the human femur. This is obtained, as known in the field, by making the nail 1 have a curvature radius of about 2500 mm, on the front-rear plane.

Moreover, the nail 1, according to the present invention, has a proximal kink of about 5° on the middle-lateral plane suitable for facilitating sideways access.

The diameter of the channel 6 is selected so as to allow the passage of the screw S and its inner wall can be either smooth or threaded, in the latter case to cooperate with a corresponding threading located on the rod of the screw S itself.

Preferably, the diameter of the channel 6 is such as to prevent the screw S from making transversal movements with respect to the axis of the channel.

In practice, the screw S must be able to be inserted into and withdrawn from the channel 6 without effort, but on the inside it must not be able to oscillate in other directions.

Of course the length of the screw that transverses the channel will be chosen in compliance with the anatomical form and dimensions of the patient's femur, in such a way that it can find grip on the cortical bone of the lesser trochanter, usually protruding from the latter for a maximum of 4-5 mm. The aim of this screw is to provide greater stability to the nail when it is subjected to axial load and/or torsional momentum.

According to an alternative embodiment of the present invention the inlet 6a is located directly on the apex of the rod 2, in correspondence with the access opening of its internal cavity 21.

This placement of the inlet opening consents direct access to the channel 6 from the same point as where the nail is inserted into the bone.

In practice it will not be necessary in the latter case to create a passage in order to reach the channel 6.

In fact, in the embodiment in which the inlet 6a to the channel 6 is placed on the lateral wall of the rod 2, the grip of the screw S is bone-nail-bone, whereas in the case where the inlet to the channel 6 is placed on the apex of rod 2, the grip on the bone of the screw S is monocortical nail-bone.

By virtue of the particular placement of the inlet 6a to the channel 6 on the apex of rod 2, the axis Y along which the channel 6 is extended always forms an acute angle β with the longitudinal axis X of the rod 2. This acute angle β lies between 15° and 45°, preferably 35°, on the front-rear plane.

Due to this angled configuration and in the presence of the tubular sleeve with thin walls of generally less than 3 mm, the outlet opening 7b can be shaped as an elongated hole in order to facilitate the transverse passage of the screw S.

Of course, when the inlet 6a to the channel 6 is placed on the apex of the rod 2, also the outlet opening 7a will coincide with the opening that is present on the apex of the tubular sleeve 5.

One should recall that in any embodiment of the present invention the openings 7a, 7b present on the tubular sleeve 5 do not require having particular dimensions, since their only function is to facilitate the transverse passage of the screw S. On the other hand, as has been stated earlier, the channel 6 must have correct dimensions in accordance with the dimensions of the screw S, to prevent any oscillation of the screw with respect to the rod.

Figure 9:
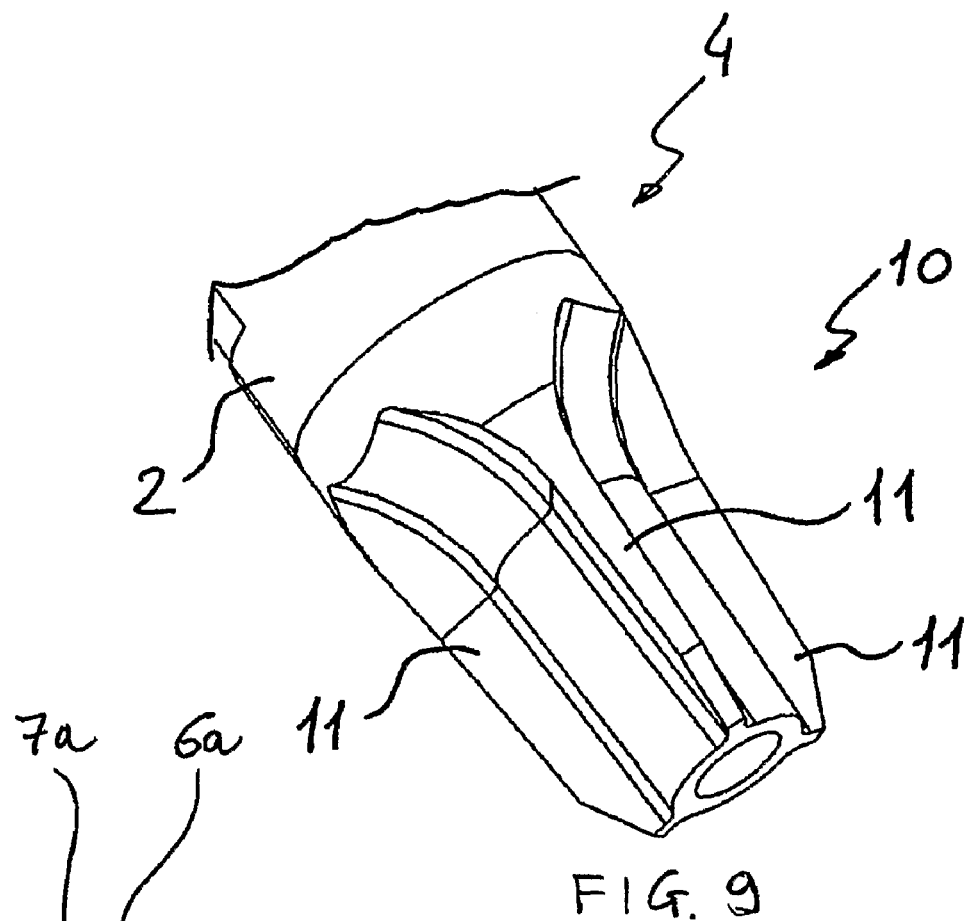
FIG. 9 illustrates a detail of the distal end of the nail according to the invention.
Figure 8:
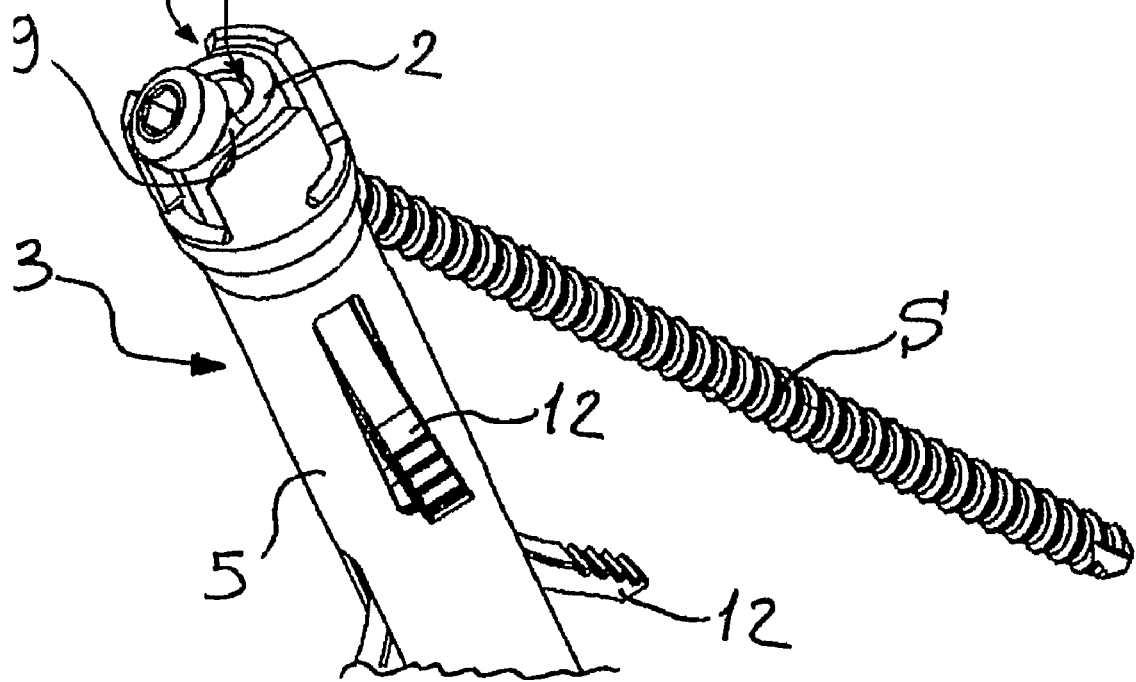
FIG. 8 illustrates a detail of the proximal end of the nail of FIG. 6 with a screw inserted.
Figure 10:
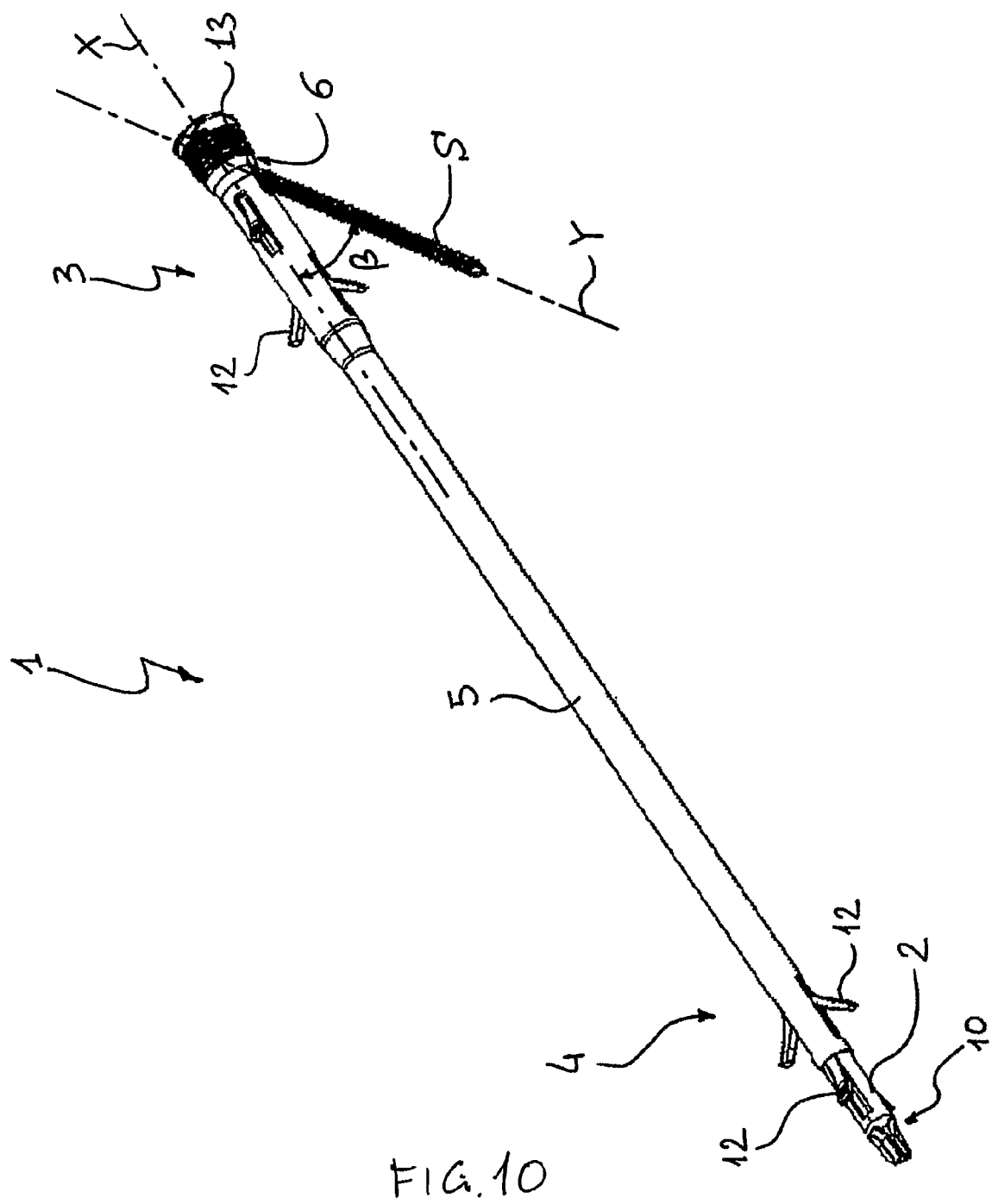
FIG. 10 illustrates the nail of FIG. 6 with a cap-screw.
Figure 11:
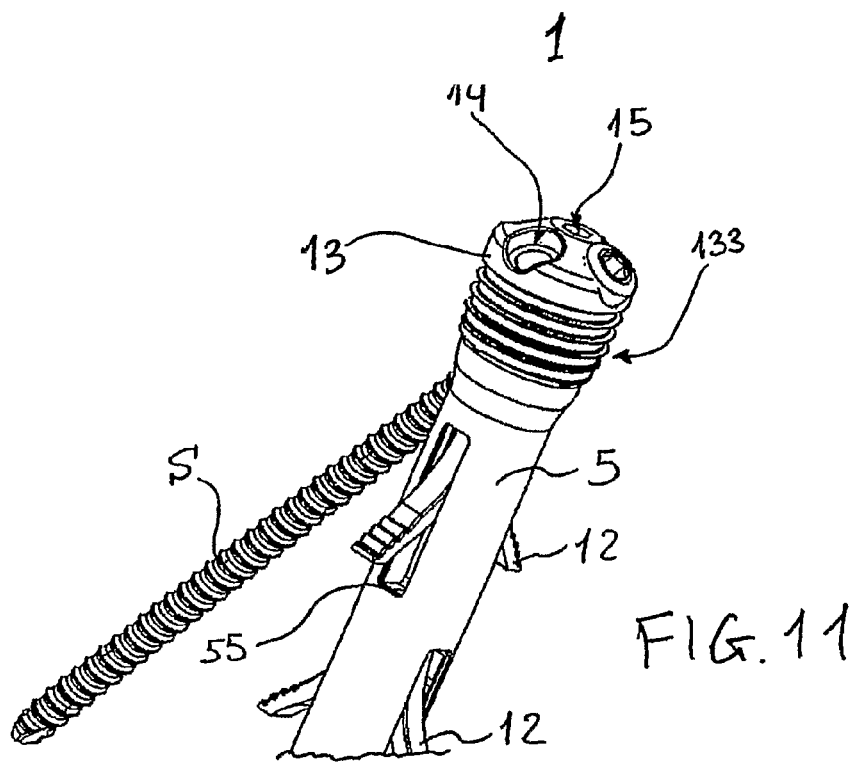
FIG. 11 illustrates a detail of the proximal end of the nail of FIG. 9.

In accordance with an embodiment of the present invention, at the proximal opening a seat 9 is formed, clearly visible in FIG. 9, shaped to receive in abutment the base of the head of the stop screw S that crosses the channel 6.

In the illustrated example, such a seat 9 is formed from a bevel formed on the rod 2 through a cut that lies on a plane normal to the longitudinal axis Y of the channel 6.

In order to allow easy fastening/unfastening of the nail 1 from the relative instruments, the use of an attachment system is foreseen, formed directly on top of the tubular sleeve 5.

In the example, the attachment system is of the bayonet type; however, any other fastening system known in the field can be used.

Figure 6A:
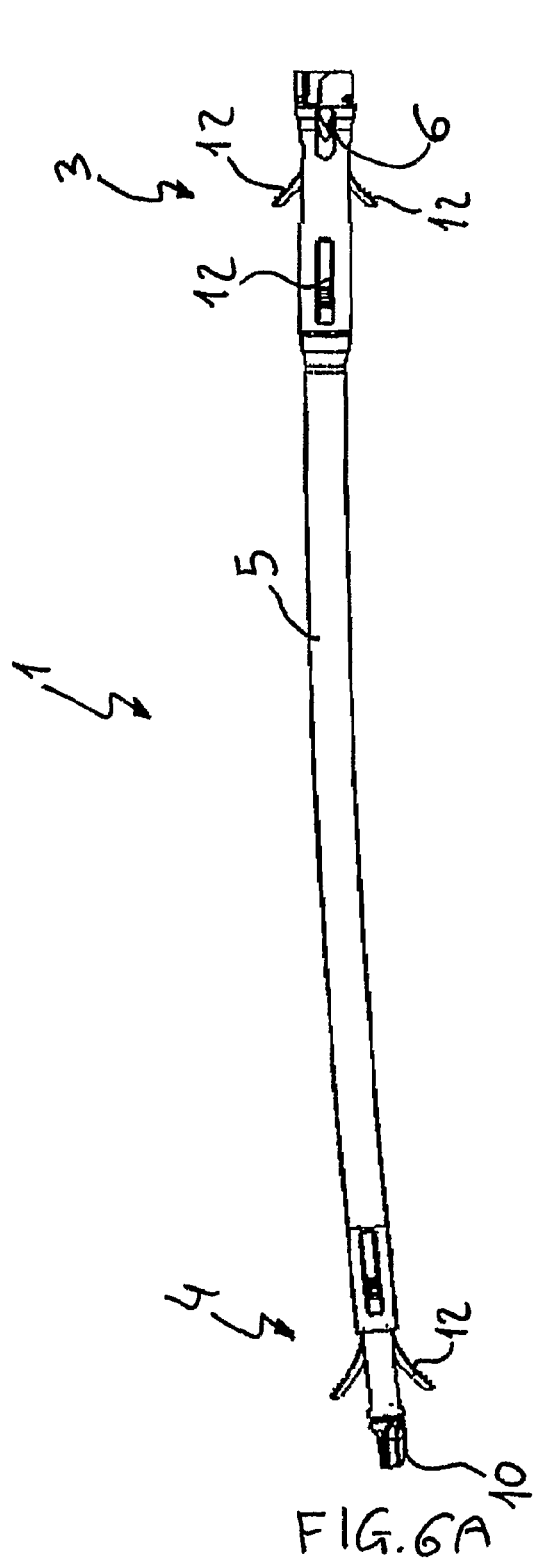
FIGS. 6A and 6B illustrate a respective different side view of the nail of FIG. 1, according to a different further embodiment.
Figure 6B:
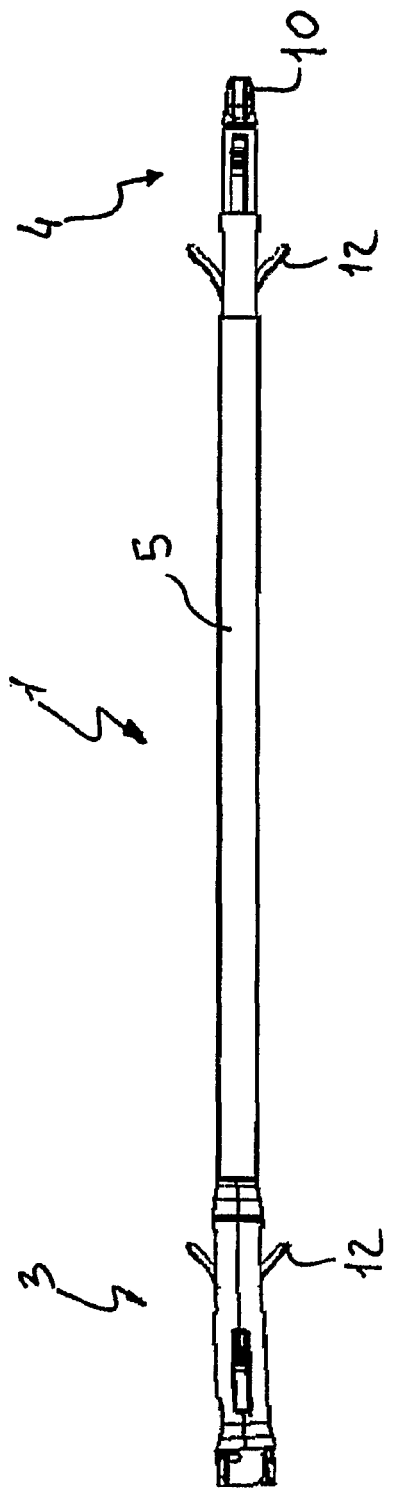
Figure 7A:
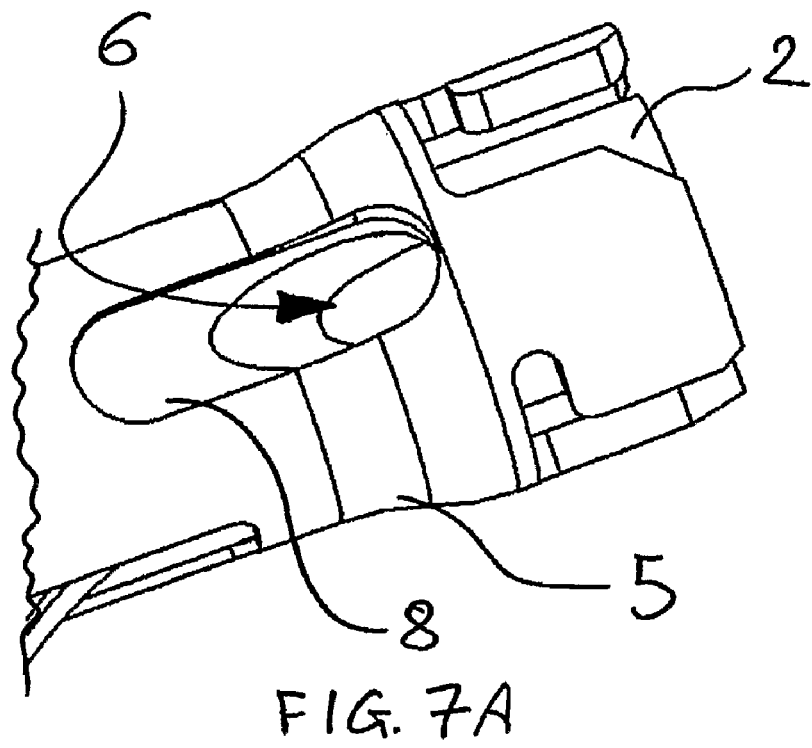
FIGS. 7A-7B illustrate different views of a detail of the proximal end of the nail of FIG. 6.
Figure 7B:
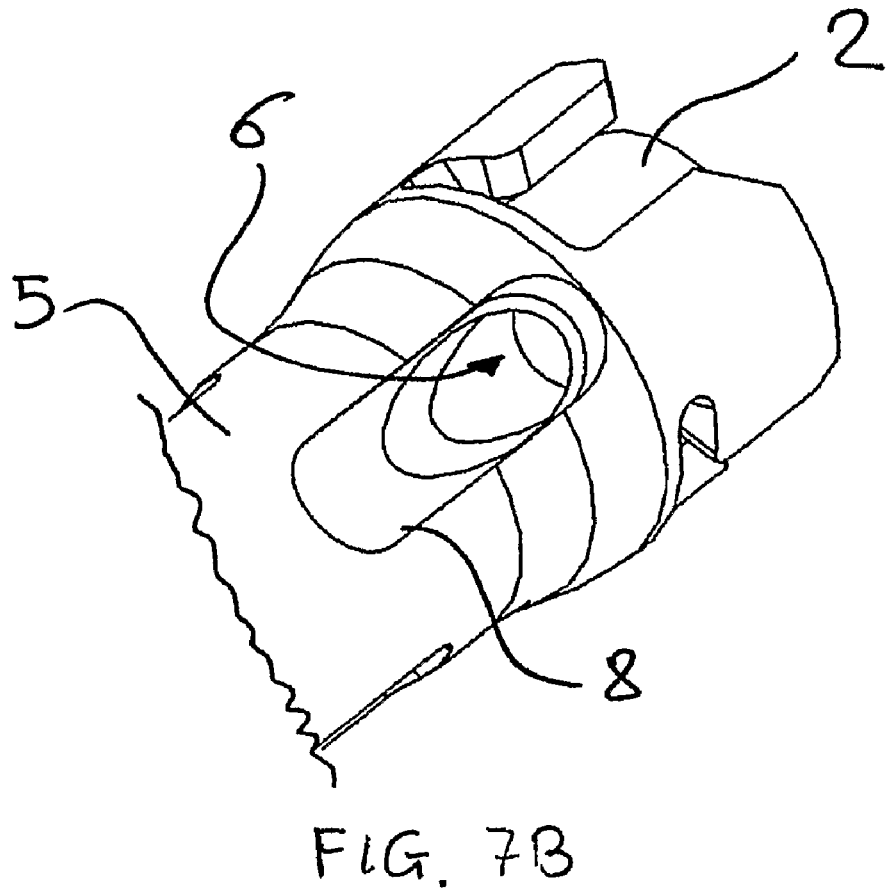

In accordance with a further embodiment of the present invention, the distal part 4 of the rod 2 of the nail 1 has a tapered configuration, indicated by 10 (FIG. 6). This tapered area 10 is provided with a plurality of ribs 11 arranged radially and extending longitudinally. In the illustrated example there are three ribs 11 arranged at 120°.

The ribs 11 located in the tapered area 10 of the distal end 4 of the rod 2 give the nail 1 better resistance to twisting torques. Moreover, in order to make it easier for the nail to penetrate inside the bone, the extreme angles of the ribs 11 can be cut, as shown in FIG. 6, so as to give the distal end 4 of the rod 2 a substantially wedge-shaped configuration. This makes the work of the operator above all easier, who hammers from the proximal end (with relative fastened instruments) to penetrate for example the spongiosa, located in the distal area of the femur, up to a distance of about 20 mm from the condyles.

Figure 12:
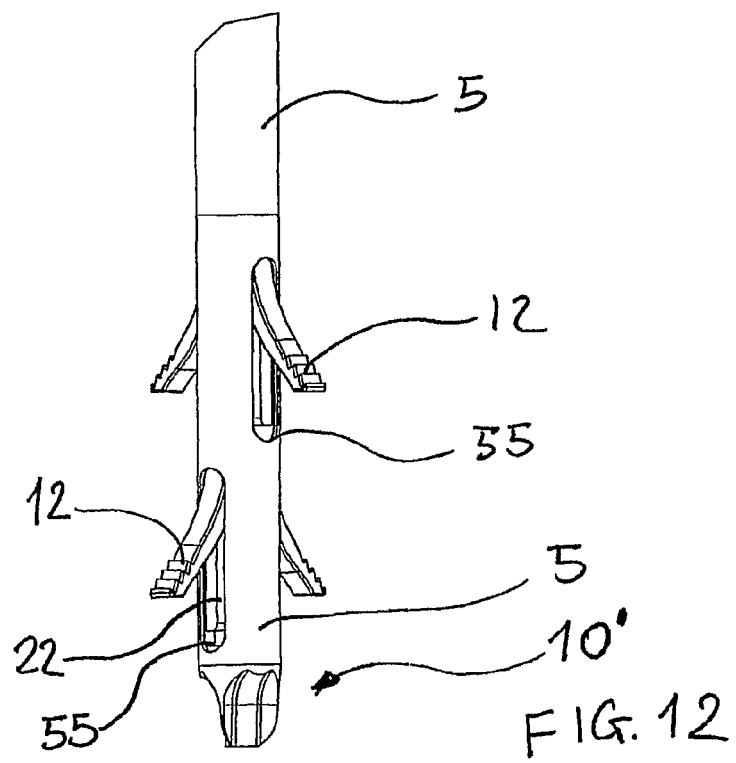
FIG. 12 shows a detail of the distal end of the nail according to a particular embodiment.

Alternatively it is also possible that there is a tapered area, indicated by 10', on the end portion of the tubular sleeve, which is located on the distal tip of the nail and configured in a way entirely equivalent with what has been described earlier. In the latter case the distal portion 4 of the rod 2 is completely placed on the internal of the tubular sleeve 5 (FIG. 12).

Basically the tip of the nail 1 is formed respectively by the distal end of the rod 2 in case the tapered area 10 is located on the rod 2, or by the distal end of the tubular sleeve 5 when the tapered area 10' is located on the tubular sleeve 5.

In accordance with a further embodiment of the present invention, the nail 1 is provided with a cap-screw 13 suitable for being fastened to the top of the tubular sleeve 5, at the proximal end 3 of the rod 2.

In the example, attachment occurs by means of a hexagon wrench to be inserted into a corresponding impression 15 formed on the top of the cap-screw 13 itself, which is fastened to the jacket by means of the bayonet system, in this way protecting the fastening system that remains inside the cap-screw.

According the present invention, the cap-screw 13 is provided with at least one hole 14 to allow the passage of the screw S. In practice, where the use of the cap-screw 13 is intended, the hole 14 becomes the inlet opening for access to the channel 6 of the screw S. Of course, the hole 14 of the cap-screw 13 must be aligned with the channel 6 to allow the screw S to reach the channel 6 through the hole 14. In this respect it is possible to foresee making many holes 14 on the same cap-screw 13 arranged so that at least one of them is always located in a position suitable for allowing the correct insertion of the screw S into the channel 6. In the illustrated example, the cap-screw 13 is provided with four holes 14 sufficient to allow the perfect alignment of one of them with the channel 6, after fastening to the tubular sleeve 5.

The use of the cap-screw 13 allows the access to the cavity located on the proximal end 3 of the rod 2 to be closed off, so as to avoid bone regrowth in the fastening area of the nail 1. In addition, it further increases the ability to withstand axial stress.

Moreover, it is preferable that the cap-screw 13 has a threaded outer surface 133 in order to guarantee further coupling with the bone when it is attached to the nail.

As can be appreciated from what has been described, the intramedullary nail according to the present invention meets the requirements and overcomes the drawbacks mentioned in the introductory part of the present description with reference to the prior art.

More particularly, thanks to the realisation of the insertion channel of the screw according to the present invention, an improvement of the torsional and axial stability of the nail itself is obtained.

Of course, a person skilled in the art can apply numerous modifications and variants to the intramedullary nail described above, in order to satisfy contingent and specific requirements, all of which are covered by the scope of protection of the invention, as defined by the following claims.

The invention claimed is:

1. A intramedullary nail to be inserted into a fractured long bone, for example a femur, comprising:
   a rod extending between a proximal part and a distal part;
   a tubular sleeve into which said rod is inserted coaxially, said tubular sleeve having an opening on its apex;
   at least a first pair of expansion means located in the distal part of said rod, said expansion means being made of a shape-memory material in order to assume a first configuration of rest in which they are arranged inside recesses in the lateral wall of the nail, and a second configuration of use in which said means are located projecting from the lateral wall of the nail;
   slots are present on the tubular sleeve in correspondence with the shape-memory means to allow for the fastening onto the bone when the means assume said second configuration of use;
   wherein said rod is of the cannulated type having an internal cavity with an opening on its apex; and
   wherein said rod comprises in correspondence with the proximal end a transversal channel for the passage of a stop screw, said tubular sleeve comprising a pair of opposite apertures placed in alignment with said channel,
   an inlet for said channel being located directly on the apex of the rod in correspondence with the opening of its internal cavity and one of said opposite aperture of the tubular sleeve coinciding with the opening that is present on the apex of the tubular sleeve; and
   wherein the distal part of the rod does not have any through-channel for a screw.

2. The intramedullary nail according to claim 1, in which the proximal end has at least a second pair of expansion means made of a shape-memory material that assume a first configuration of rest in which these means are arranged inside recesses in the lateral wall of the nail, and a second configuration of use in which said means project from the lateral wall of the nail to fasten onto the bone.

3. The intramedullary nail according to claim 1, in which said channel is extended along an axis which forms an acute angle (β) with the longitudinal axis of the rod.

4. The intramedullary nail according to claim 1, wherein in correspondence with said inlet on the apex of the nail a seat is formed, configured to receive in abutment the base of the head of the screw.

5. The intramedullary nail according to claim 1, wherein the distal part of the rod of the nail has a predetermined tapered area provided with a plurality of ribs arranged radially and extending longitudinally.

6. The intramedullary nail according to claim 1, comprising a cap-screw suitable for being fastened by means of a bayonet type attachment to the apex of the nail.

7. The intramedullary nail according to claim 6, wherein said cap-screw has a threaded external surface that can attach itself to the bone when the cap-screw is attached to the nail.

8. The intramedullary nail according to claim 6, wherein said cap-screw comprises at least one through-hole positioned so as to be in alignment with said channel when the cap-screw is attached to the nail.

9. A device for treatment of bone fractures comprising an intramedullary nail which comprises:
   a rod extending between a proximal part and a distal part;
   a tubular sleeve into which said rod is inserted coaxially, said tubular sleeve having an opening on its apex;

at least a first pair of expansion means located in the distal part of said rod, said expansion means being made of a shape-memory material in order to assume a first configuration of rest in which they are arranged inside recesses in the lateral wall of the nail, and a second configuration of use in which said means are located projecting from the lateral wall of the nail;

wherein slots are present on the tubular sleeve in correspondence with the shape-memory means to allow for the fastening onto the bone when the means assume said second configuration of use;

wherein said rod is of the cannulated type having an internal cavity with an opening on its apex; and wherein said rod comprises in correspondence with the proximal end a transversal channel for the passage of a stop screw, said tubular sleeve comprising a pair of opposite apertures placed in alignment with said channel an inlet for said channel bein located directly on the apex of the rod in correspondence with the opening of its internal cavity and one of said opposite aperture of the tubular sleeve coinciding with the opening that is present on the apex of the tubular sleeve, an outlet for said channel being located on the proximal part of said rod; and a straight screw suitable for being inserted into said channel and comprising a threading that permits fastening to the bone.

10. The device according to claim 9, in which said screw(s) presents a threading that can combine with a corresponding threading on the internal wall of the channel.

* * * * *